United States Patent [19]

Freeburne et al.

[11] Patent Number: 5,189,193
[45] Date of Patent: Feb. 23, 1993

[54] PROCESS FOR PREPARATION OF CYCLIC ORGANOHYDROSILOXANES

[75] Inventors: Steven K. Freeburne, Edgewood; David E. Puckett, Taylor Mill, both of Ky.

[73] Assignee: Dow Corning Corporation, Midland, Mich.

[21] Appl. No.: 937,089

[22] Filed: Aug. 31, 1992

[51] Int. Cl.$^5$ .................................. C07F 7/08
[52] U.S. Cl. ........................................ 556/451
[58] Field of Search ........................... 556/451

[56] References Cited

U.S. PATENT DOCUMENTS

| | | | |
|---|---|---|---|
| 3,484,468 | 12/1969 | Curry | 260/448.2 |
| 3,714,213 | 1/1973 | Miller et al. | 260/448.2 E |
| 4,539,418 | 9/1985 | Takago et al. | 556/451 |
| 4,895,967 | 1/1990 | Givelio et al. | 556/451 |

OTHER PUBLICATIONS

Sauer et al., J. Am. Chem. Soc. 68:962 (1946).

*Primary Examiner*—Paul F. Shaver
*Attorney, Agent, or Firm*—William F. Boley

[57] ABSTRACT

The present invention is a process for preparation of cyclic organohydrosiloxanes. The process comprises contacting an organohydrodihalosilane with a substantially stoichiometric quantity of water to form a mixture containing cyclic and short-chain linear organohydrosiloxanes. This mixture is distilled to separate the cyclic and short-chain linear organohydrosiloxanes from other components of the mixture. The separated cyclic and short-chain linear organohydrosiloxanes are then contacted with an additional quantity of water to effect hydrolysis and condensation of the short-chain linear organohydrosiloxanes to higher molecular weight linear organohydrosiloxanes which are easily separated from the cyclic organohydrosiloxanes by a second distillation step.

11 Claims, No Drawings

PROCESS FOR PREPARATION OF CYCLIC ORGANOHYDROSILOXANES

BACKGROUND OF INVENTION

The present invention is a process for preparation of cyclic organohydrosiloxanes. The process comprises contacting an organohydrodihalosilane with a substantially stoichiometric quantity of water to form a mixture containing cyclic and short-chain linear organohydrosiloxanes. This mixture is distilled to separate the cyclic and linear organohydrosiloxanes from other components of the mixture. The separated cyclic and linear organohydrosiloxanes are then contacted with an additional quantity of water to effect hydrolysis and condensation of the linear organohydrosiloxanes to higher molecular weight linear organohydrosiloxanes which are easily separated from the cyclic organohydrosiloxanes by a second distillation step.

The present process provides cyclic organohydrosiloxanes that are essentially free of linear organohydrosiloxanes. The cyclic organohydrosiloxanes formed by the present process are useful reactive intermediates that can be reacted with, for example, polydimethylsiloxanes to form block copolymers and with unsaturated polyethers to form surfactants, compatibilizing agents, and stabilizing agents. The cyclic organohydrosiloxanes formed by the present process are also useful as a cross-linker for other siloxanes to form silicone elastomers and gels.

Sauer et al., J. Am. Chem. Soc. 68:962 (1946). observed that when methyldichlorosilane was reacted with water a highly viscous oil was formed which within a few minutes was transformed into a rubbery gel. Sauer et al. teach that the formation of this high polymer can be avoided by running the hydrolysis process at low temperature in an ether solution. This process suffers both from the need for a low temperature to be maintained and from the use of a highly flammable solvent.

Curry, U.S. Pat. No. 3,484,468, issued Dec. 16, 1969, teaches making cyclic methylhydrosiloxanes by reacting a tertiary alcohol with an organohydrodihalosilane in the present of a solvent such as benzene. This process is less than optimal because it generates a chlorinated hydrocarbon as a by-product that has little value. Furthermore, the use of a tertiary alcohol as the source of oxygen is far more expensive than the water required in the present process.

Miller et al., U.S. Pat. No 3,714,213, issued Jan. 30, 1973, teaches a process for making cyclic organohydrosiloxanes by catalytically cracking and cyclizing linear polysiloxanes containing methyl substituents, hydrogen substituents, and high molecular weight chain terminal groups, such as hexyldimethysilyl groups. A major drawback to this process is the synthesis of the linear polysiloxanes with the high molecular weight chain terminal groups.

The present process provides for high yields of essentially pure cyclic organohydrosiloxanes without the use of low temperatures, solvents, catalysts, and chain terminators, as required by processes taught in the cited

SUMMARY OF INVENTION

The present invention is a process for preparation of cyclic organohydrosiloxanes. The process comprises contacting an organohydrodihalosilane with a substantially stoichiometric quantity of water to form a mixture containing cyclic and short-chain linear organohydrosiloxanes. This mixture is distilled to separate the cyclic and short-chain linear organohydrosiloxanes from other components of the mixture. The separated cyclic and short-chain linear organohydrosiloxanes are then contacted with an additional quantity of water to effect hydrolysis and condensation of the short-chain linear organohydrosiloxanes to higher molecular weight linear organohydrosiloxanes which are easily separated from the cyclic organohydrosiloxanes by a second distillation step.

DESCRIPTION OF INVENTION

The present invention is a process for preparation of cyclic organohydrosiloxanes. The process comprises:
(A) contacting an organohydrodihalosilane described by formula

$$RHSiX_2$$

with a substantially stoichiometric quantity of water at a temperature within a range of about 0° C. to 50° C. to form a first mixture;
(B) distilling the first mixture to recover a second mixture comprising cyclic organohydrosiloxanes and short-chained polyorganohydrosiloxanes;
(C) contacting the second mixture with water to effect polymerization of the short-chained polyorganohydrosiloxane to long-chain polyorganohydrosiloxanes and forming a third mixture;
(D) distilling the third mixture to recover cyclic organohydrosiloxanes described by formula

$$(RHSiO)_n;$$

where each R is a radical independently selected from a group consisting of alkyls comprising one to 20 carbon atoms, alkenyls comprising one to 20 carbon atoms, and aryls; X is a halogen; and n=3 to 12.

The contacting of the organohydrodihalosilanes with a substantially stoichiometric quantity of water can be effected in any standard reactor suitable for the hydrolysis of halosilanes. The process can be conducted as a continuous process or as a batch process. The reactor can be, for example, a plug-flow type reactor or a continuous-stir type reactor.

The organohydrodihalosilanes useful in the present invention are described by the formula $RHSiX_2$, where each R is a radical independently selected from a group consisting of alkyls comprising one to 20 carbon atoms, alkenyls comprising one to 20 carbon atoms, and aryls The radical R can be, for example, methyl, ethyl, propyl, butyl, tertbutyl, heptyl, hexyl, vinyl, allyl, hexenyl, phenyl, tolyl, xylyl, and naphthyl. Preferred is when R is methyl.

The organohydrodihalosilane also has two substituents X, were each X is a halogen. The halogen X can be chlorine, iodine, fluorine, or bromine. Preferred is when X is chlorine.

The organohydrodihalosilane is contacted with a substantially stoichiometric quantity of water. In the present process, a stoichiometric quantity of water is considered to be one mole of water per mole of organohydrodihalosilane. By "substantially stoichiometric" it is meant that there is present in the process about 0.8 mole of water to 1.2 mole of water per mole of organohydrodihalosilane. Preferred is when the process is run with 0.9 to less than 1.0 mole of water per mole of organohydrodihalosilane.

Contact of the organohydrodihalosilane with a substantially stoichiometric quantity of water is effected at a temperature of about 0° C. to 50° C. Preferred is when the process is run at a temperature within a range of about 10° C. to 30° C. The temperature of the process can be maintained by standard means, for example, a heating mantle or jacket surrounding the exterior of the reactor.

The product of contacting the organohydrodihalosilane with the substantially stoichiometric quantity of water is a mixture comprising cyclic organohydrosiloxanes, short-chained linear chlorine end-terminated polyorganohydrosiloxanes, and, typically, long-chained linear chlorine end-terminated polyorganohydrosiloxanes and any excess water. By the term "short-chained" it is meant those linear chlorine end-terminated polyorganohydrosiloxanes having a molecular weight sufficiently close to the cyclic organohydrosiloxanes to make separation by distillation difficult. The chlorine end-terminated linear polyorganohydrosiloxanes for purpose of brevity are hereafter referred to as short-chain or long-chain polyorganohydrosiloxanes.

Hydrogen chloride gas is generated as a by-product of contacting the organohydrodihalosilane with a substantially stoichiometric quantity of water. If desired, this hydrogen chloride gas can be recovered from the process by standard methods and used as a feed to other processes.

The first mixture is distilled by standard methods to recover a second mixture comprising cyclic organohydrosiloxanes and short-chained polyorganohydrosiloxanes. Distillation can be effected by standard methods for separating liquid mixtures, where the cyclic organohydrosiloxanes and short chained polyorganohydrosiloxanes are recovered from the vapor phase exiting the distillation apparatus. Distillation can be effected by, for example, flash distillation. The optimal temperature and pressure for distilling the first mixture will depend upon the particular organohydrodihalosilane employed in the process and the resultant products.

The second mixture containing the cyclic organohydrosiloxanes and short-chained polyorganohydrosiloxanes is contacted with additional water to effect polymerization of the short-chained polyorganohydrosiloxanes to long-chained polyorganohydrosiloxanes and form a third mixture. The term "long-chained" polyorganohydrosiloxanes refer to linear polyorganohydrosiloxanes having a molecular weight sufficiently different from the molecular weight of the cyclic organohydrosiloxanes to allow for separation by distillation.

The amount of water contacted with the second mixture to create the third mixture can be any amount sufficient to cause conversion of the short-chained polyorganohydrosiloxanes to long-chained polyorganohydrosiloxanes. Generally, about 0.01 to 10 volumes of water per volume of the second mixture is considered useful. Preferred, is when about 0.05 to 1.0 volumes of water per volume of the second mixture is used.

The third mixture is distilled to recover cyclic organohydrosiloxanes. In a preferred process, before the third mixture is distilled, the third mixture is separated from any water present. Separation of the water from the third mixture can be effected by standard methods for effecting phase separation of siloxanes and water, for example, gravity separation of the phases followed by decanting of a phase. Distillation of the third mixture can be by standard methods as described for distilling of the first mixture.

Distillation of the third mixture also results in a component containing long-chained polyorganohydrosiloxanes. These long-chained polyorganohydrosiloxanes can be recovered and used as is or end-cap by standard methods to form stable end-capped long-chained polyorganohydrosiloxanes.

The cyclic organohydrosiloxanes recovered from the present process are described by the formula $(RHSiO)_n$, where R is as previously described and n is an integer from three to 12. Preferred is when n is an integer from four to eight. Most preferred is when R is methyl and n is an integer from four to eight.

Generally, it is preferred that the cyclic organohydrosiloxanes recovered by distillation of the third mixture be washed with one or more additional quantities of water to remove any residual chlorine. The number of washes and volume of water used will depend upon the residual chlorine present in the cyclic organohydrosiloxanes and the required stability of the cyclic organohydrosiloxanes.

The following example is provided to illustrate the present invention. This example is not intended to limit the scope of the claims herein.

Example. Methyldichlorosilane was contacted with water and cyclic methylhydrosiloxanes isolated from the resultant hydrolysate. The process was conducted in a 1.1 cm × 33.5 cm teflon reactor operated in a plug-flow mode. About 10.5 mL/min. of methyldichlorosilane ($MeHSiCl_2$) and 1.79 mL/min. of water were fed into the reactor. The temperature of the reactor was maintained at about 20° C. The product from the reactor was collected and flash distilled at a temperature of about 170° C. and at a pressure of about 50 mm Hg to separated a vapor fraction containing cyclic methylhydrosiloxanes and short-chained linear polymethylhydrosiloxanes. The vapor fraction was condensed in a standard laboratory condenser and collected. The resultant liquid mixture comprising the cyclic methylhydrosiloxanes and short-chained linear polymethylhydrosiloxanes was mixed with water at a ratio of one volume of water per ten volumes of siloxanes for one minute. The water phase was allowed to gravity separate and then separated from the siloxane phase. The siloxane phase was flash distilled at temperature of about 125° C. and at a pressure of about 50 mm Hg to separate a vapor fraction containing the cyclic methylhydrosiloxanes The vapor fraction was condensed in a standard laboratory condenser and analyzed by gas chromatography (GC) using a mass spectrometer (MS) as detector. This condensed vapor fraction was determined by GC/MS to be a pure mixture of cyclic methylhydrosiloxanes of formula $(MeHSiO)_n$, where n=3 to 8.

We claim:

1. A process of cyclic organohydrosiloxanes, the process comprising:

(A) contacting an organohydrodihalosilane described by formula $$RHSiX_2$$

with a substantially stoichiometric quantity of water at a temperature within a range of about 0° C. to 50° C. to form a first mixture;

(B) distilling the first mixture to recover a second mixture comprising cyclic organohydrosiloxanes and short-chained polyorganohydrosiloxanes;

(C) contacting the second mixture with water to effect polymerization of the short-chained polyorganohydrosiloxane to long chain polyorganohydrosiloxanes and forming a third mixture;

(D) distilling the third mixture to recover cyclic organohydrosiloxanes described by formula $(RHSiO)_n$;

where each R is a radical independently selected from a group consisting of alkyls comprising one to 20 carbon atoms, alkenyls comprising one to 20 carbon atoms, and aryls; X is a halogen; and n=3 to 12.

2. A process according to claim 1, where R is methyl.

3. A process according to claim 1, where X is chlorine.

4. A process according to claim 1, where a substantially stoichiometric quantity of water is about 0.8 mole of water to 1.2 mole of water per mole of organohydrodihalosilane.

5. A process according to claim 1, where a substantially stoichiometric quantity of water is about 0.9 mole of water to less than 1.0 mole of water per mole of organohydrodihalosilane.

6. A process according to claim 1, where the temperature is within a range of about 10° C. to 30° C.

7. A process according to claim 1, where hydrogen chloride gas generated by the process is recovered and used as a feed to another process.

8. A process according to claim 1, where the second mixture is contacted with about 0.01 to 10 volumes of water per volume of the second mixture.

9. A process according to claim 1, where the second mixture is contacted with about 0.05 to 1.0 volume of water per volume of the second mixture.

10. A process according to claim 1, where n=4 to 8.

11. A process for preparation of cyclic organohydrosiloxanes, the process comprising:

(A) contacting an organohydrodihalosilane described by formula $RHSiX_2$ with about 0.8 mole of water to 1.2 mole of water per mole of organohydrodihalosilane at a temperature within a range of about 10° C. to 30° "C. to form a first mixture;

(B) distilling the first mixture to recover a second mixture comprising cyclic organohydrosiloxanes and short-chained polyorganohydrosiloxanes;

(C) contacting the second mixture with about 0.05 to 1.0 volume of water per volume of the second mixture to effect polymerization of the short chained polyorganohydrosiloxane to long-chain polyorganohydrosiloxanes and forming a third mixture;

(D) distilling the third mixture to recover cyclic organohydrosiloxanes described by formula $(RHSiO)_n$;

where R is methyl, X is chlorine, and n=4 to 8.

* * * * *